US011536645B2

(12) United States Patent
Azar et al.

(10) Patent No.: US 11,536,645 B2
(45) Date of Patent: Dec. 27, 2022

(54) DETECTING BACKSCATTER FROM DROPS DISPENSED FROM A HANDHELD DROPPER AND ASSOCIATED SYSTEMS, DEVICES, AND METHODS

(71) Applicant: Twenty Twenty Therapeutics LLC, South San Francisco, CA (US)

(72) Inventors: Dimitri Azar, San Francisco, CA (US); Supriyo Sinha, Menlo Park, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 130 days.

(21) Appl. No.: 16/871,516

(22) Filed: May 11, 2020

(65) Prior Publication Data

US 2020/0363313 A1     Nov. 19, 2020

Related U.S. Application Data

(60) Provisional application No. 62/847,179, filed on May 13, 2019.

(51) Int. Cl.
*G01N 15/14* (2006.01)
*A61F 9/00* (2006.01)
*A61M 5/168* (2006.01)

(52) U.S. Cl.
CPC ....... *G01N 15/1434* (2013.01); *A61F 9/0008* (2013.01); *G01N 15/1456* (2013.01); *A61M 5/1689* (2013.01); *A61M 2205/3306* (2013.01)

(58) Field of Classification Search
None
See application file for complete search history.

(56) References Cited

U.S. PATENT DOCUMENTS 5,012,496 A * 4/1991 Weinreb ............... A61F 9/0008
                                                377/6
5,186,057 A   2/1993 Everhart
(Continued)

FOREIGN PATENT DOCUMENTS

CN    107106768 A  *  8/2017  ............. A61M 5/14
DE      3726847 A1  *  2/1989  .......... A61M 5/1684

OTHER PUBLICATIONS

Trondlea J. et al. "Non-contact optical sensor to detect free flying droplets in the nanolitre range"; Sensors and Actuators A 158 (2010); Publication [online]. Feb. 11, 2010 [retrieved Jul. 9, 2020]. Retrieved from the Internet: <URL: https://www.journals.elsevier.com/sensors-and-actuators-a-physical>; pp. 254-262.
(Continued)

*Primary Examiner* — Rufus L Phillips
(74) *Attorney, Agent, or Firm* — Haynes and Boone, LLP

(57) ABSTRACT

Devices, systems, and associated methods for detecting drops dispensed by a dropper are provided. For example, a drop detection device may include a light source and a light detector configured to be coupled to a drop dispenser such that the light source and light detector are disposed proximal of a distal dispensing tip of the drop dispenser. The light detector may be configured to receive a reflected portion of a beam of light from the light source, which is reflected by a drop dispensed through the dispensing tip of the drop dispenser. In some embodiments, a processing circuit is configured to analyze a signal provided by the light detector to detect the dispensed drop.

17 Claims, 12 Drawing Sheets

(56) References Cited

U.S. PATENT DOCUMENTS

| | | |
|---|---|---|
| 10,152,867 B2 | 12/2018 | Fateh |
| 2009/0227939 A1 | 9/2009 | Mernoe et al. |
| 2009/0247865 A1 | 10/2009 | Spohn et al. |
| 2014/0228783 A1 | 8/2014 | Kraft |
| 2014/0276476 A1* | 9/2014 | Fateh .................... A61F 9/0026 604/290 |
| 2015/0289805 A1* | 10/2015 | Eaton ..................... G16H 20/13 604/290 |
| 2018/0008459 A1 | 1/2018 | Kinast et al. |
| 2018/0095022 A1 | 4/2018 | Petersen |

OTHER PUBLICATIONS

International Searching Authority, International Search Report and Written Opinion of the International Searching Authority, PCT/US2020/032425, dated Aug. 11, 2020, 17 pages.

* cited by examiner

DETECTING BACKSCATTER FROM DROPS DISPENSED FROM A HANDHELD DROPPER AND ASSOCIATED SYSTEMS, DEVICES, AND METHODS

CROSS-REFERENCE TO RELATED APPLICATIONS

The present application claims the benefit of and priority to U.S. Provisional Patent Application No. 62/847,179, filed May 13, 2019, the entirety of which is hereby incorporated by reference.

TECHNICAL FIELD

The subject matter described herein relates to devices and methods for detecting drops dispensed from a dropper. For example, embodiments of the present disclosure include a light source and a light detector configured to detect backscatter from a drop dispensed from a handheld dropper.

BACKGROUND

One challenge in the treatment of eye-related disorders, such as glaucoma and dry-eye, is maintaining compliance with dosage requirements and schedules. For example, some disorders require strict treatment schedules in which multiple applications of a drug or pharmaceutical agent (e.g., eye drops) are required at specific time windows throughout the day. When evaluating the effectiveness of a prescribed treatment regimen, it is desirable to determine whether the patient has been complying with the prescribed treatment schedule.

To track compliance and usage history of medication, it is desirable to be able to track and record when medication is being administered. For example, medication may be in the form of eye drops that are administered or dispensed with a handheld dropper, with the dosage and frequency set forth in a prescription provided by a physician. Data indicating administration of the medication (e.g., frequency, time of administration) can be used by the patient or eye care practitioner to determine the efficacy of the medication. In some aspects, for example, the data can be used to determine whether the patient's condition is not responding because the medication is not effective or because the patient is not taking the medication as directed.

SUMMARY

Aspects of the present disclosure provide devices, systems, and associated methods for the detection of a dispensed drop by detecting light scattered by the drop. For example, in some embodiments of the present disclosure, a drop detection device comprises a light source configured to emit a beam of light and a light detector configured to detect a scattered portion of the beam of light. The light source and light detector are positioned proximally of a distal dispensing tip of a drop dispenser so that the components of the drop detection device do not interfere with the application of the drop.

According to one embodiment of the present disclosure, a device for detecting a drop dispensed by a drop dispenser includes: a housing configured to couple to the drop dispenser; a light source coupled to the housing and configured to emit a beam of light toward the drop dispensed by the drop dispenser; a processing circuit; and a light detector coupled to the housing and in communication with the processing circuit. The light detector is configured to: receive a portion of the beam of light reflected by the drop; and provide, to the processing circuit, a signal indicating an amount of reflected light received over a period of time. The processing circuit is configured to detect the drop based on the signal, and the light source and the light detector are coupled to the housing such that the light source and the light detector are positioned proximally of a distal end of the drop dispenser when the drop dispenser is coupled to the housing.

In some embodiments, the light source comprises at least one of a laser diode and a light-emitting diode. In some embodiments, the light detector comprises a photodiode. In some embodiments, the light detector comprises a bandpass filter and a focusing lens. In some embodiments, the light source is coupled to the housing such that, when the housing is coupled to the drop dispenser, the light source is oriented to emit the beam of light along a first axis at a first oblique angle relative to a dispensing axis of the drop dispenser, and wherein the light detector is coupled to the housing such that, when the housing is coupled to the drop dispenser, the light detector is oriented to receive the portion of the beam of light along a second axis at a second oblique angle relative to the dispensing axis of the drop dispenser. The first axis, the second axis, and the dispensing axis intersect at an interrogation point located distally of a dispensing tip of the drop dispenser, in some embodiments.

In some aspects, the housing is configured to engage a lip of the drop dispenser. In other aspects, the housing is coupled to the drop dispenser such that a cap of the drop dispenser can be removed and replaced without removing the drop dispenser. In still other aspects, the processing circuit is configured to detect the drop by determining that an amplitude of the signal exceeds a threshold for a predetermined amount of time.

According to another embodiment of the present disclosure, a method for detecting a drop dispensed by a drop dispenser includes: emitting, by a light source coupled to the drop dispenser and positioned proximal of a distal end of the drop dispenser, a beam of light toward the drop; receiving, by a light detector coupled to the drop dispenser and positioned proximal of the distal end of the drop dispenser, a portion of the beam of light reflected by the drop; providing, by the light detector, a signal indicating an amount of reflected light received by the light detector over a period of time; and analyzing, by a processing component in communication the light detector, the signal to detect the drop.

In some embodiments, emitting the beam of light comprises emitting the beam of light using at least one of a laser diode or a light-emitting diode. In some embodiments, receiving the portion of the beam of light comprises receiving the portion of the beam of light using a photodiode. In some embodiments, the light detector comprises a bandpass filter and a focusing lens. In some embodiments, emitting the beam of light comprises emitting the beam of light along a first axis at a first oblique angle relative to a dispensing axis of the drop dispenser, and wherein receiving the portion of the beam of light comprises receiving the portion of the beam of light along a second axis at a second oblique angle relative to the dispensing axis of the drop dispenser. The first axis, the second axis, and the dispensing axis intersect at an interrogation point located distally of a dispensing tip of the drop dispenser, in some embodiments. In some embodiments, analyzing the signal to detect the drop comprises determining that an amplitude of the signal exceeds a threshold for a predetermined amount of time.

According to another embodiment of the present disclosure, an apparatus, comprising: a housing comprising a cavity configured to receive a drop dispenser; a light source mounted on a housing and oriented at a first oblique angle relative to a central axis of the housing to emit a beam of light along a first axis; a photodetector mounted on the housing and oriented at a second oblique angle relative to the central axis of the housing to receive scattered light along a second axis, wherein the first axis, second axis, and central axis intersect at an interrogation point; a processor coupled to the housing and in communication with the photodetector; and a battery coupled to the housing and configured to provide power to the processor, the photodetector, and the light source.

In some embodiments, the housing comprises an annular shape, and wherein the cavity comprises a lumen of the annular housing. In some embodiments, the apparatus further comprises a feedback device in communication with the processor and configured to provide an indication that a drop has been detected. In some embodiments, the housing comprises one or more distally-extending positioning arms arranged to provide access to a cap of the drop dispenser when the drop dispenser is coupled to the apparatus.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
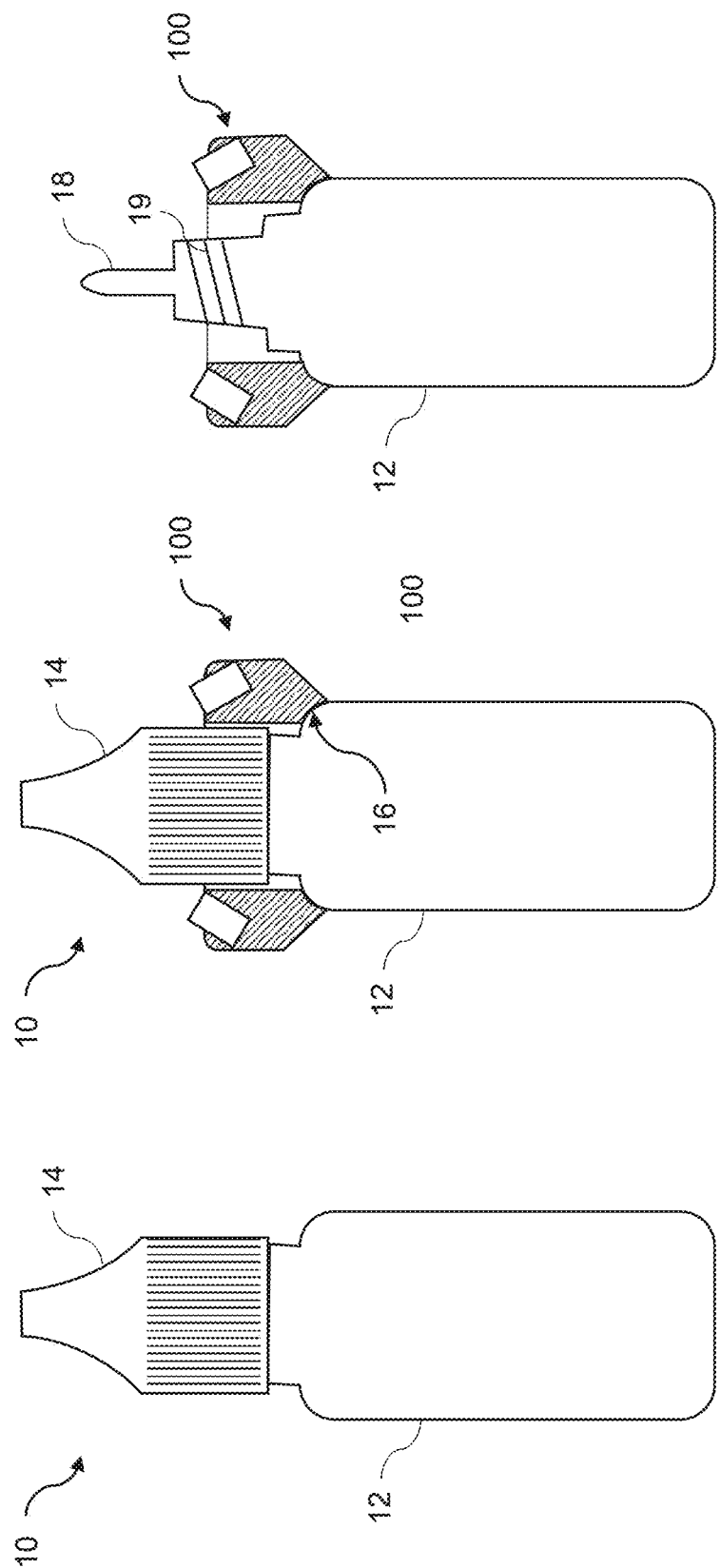
FIG. 1A is a side view of a drop dispenser, according to an embodiment of the present disclosure.
FIG. 1B is a partial cutaway view of a drop dispenser with a drop detection device, according to an embodiment of the present disclosure.
FIG. 1C is a partial cutaway view of a drop dispenser with a drop detection device, according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

To accurately track or monitor application of medication, it may be desirable that the medication administration and tracking be relatively simple. In the case of eye drops, instead of having the user record in a notebook or an app when they are applying the medication, it may be preferred to have the dropper measure the application of the droplet and then record and/or send this information with a timestamp (e.g., securely with an application, such as a mobile application on a mobile computing device).

An exemplary method to measure and/or detect the administration of a drop can include using a light transmitter and light detector located on opposite sides with respect to the drop, such that the transmitter-detector axis is perpendicular to the dispensing axis. In such a way, the difference in transmission seen by the detector as the droplet enters the field of view could be analyzed to determine if a drop is seen. However, this perpendicular arrangement of hardware may cause the hardware of the dropper to extend beyond the tip of the bottle. This may be problematic for at least two reasons. First, there is limited space between the dropper and the eye. Second, it can be difficult to remove and reattach the cap of the dropper bottle if the hardware extends beyond the dispensing tip. The ability to remove and reattach the cap may be desirable to maintain the sterility of the dispensing tip. Accordingly, embodiments of the present disclosure present drop detection devices and associated methods and systems that include a light source and light detector positioned and arranged with respect to a dropper to detect backscatter from a dispensed drop such that the light source, light detector, and associated components of the drop detection device do not extend beyond (e.g., distally of) the dispensing tip of the dropper.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIGS. 1A-1C depict various configurations of an eye dropper 10 or dispenser and a drop detection device 100, according to some embodiments of the present disclosure. In FIG. 1A, an eye dropper is shown, according to some embodiments of the present disclosure. The eye dropper 10 includes a reservoir 12 and a cap 14 attached to a top portion or distal portion of the reservoir 12. The reservoir 12 may be a plastic container or receptacle that holds a fluid, such as a pharmaceutical agent. For example, the reservoir 12 may hold a drug or pharmaceutical agent for treating one or more eye disorders, such as dry eye, glaucoma, etc. The cap 14 may be removably coupled to the reservoir 12 via screw threads 19, as shown in FIG. 1C.

FIGS. 1B and 1C show the eye dropper 10 with a cross-sectional view of the drop detection device 100, in which the drop detection device 100 is coupled to the eye dropper 10 such that the cap 14 can be removed and replaced while the device 100 is coupled to the eye dropper 10. In other embodiments, the drop detection device 100 may form part of a cap or dispenser coupled to the reservoir 12. The device 100 is coupled to the dropper 10 to interface with a lip 16 of the dropper 10 to maintain the device 10 at a relatively fixed or stable location with respect to the dispensing tip 18. However, in other embodiments, the device 10 may couple to other parts or regions of the dropper 10, such as the middle of the reservoir 12, the threads 19, the dispensing tip 19, or any other suitable portion of the dropper 10. In some embodiments, the device 100 is not coupled to the dropper 10, but is used separately from the dropper 10 to detect a drop. With the cap 14 removed, the threads 19 and dispensing tip 19 of the dropper 10 are exposed such that drops can be dispensed to a patient's eye.

In some embodiments, the reservoir 12, threads 19, and dispensing tip 18 are molded or formed as a single integral body. In other embodiments, the reservoir 12 and dispensing tip 18 may comprise separately formed pieces (e.g., of plastic) that are coupled or joined together using adhesives, interference fits, heat welds, or any other suitable means of coupling. In some embodiments, one or more components of the dropper 10 and/or the cap 14 comprise non-plastic materials, such as glass or metal.

Figure 2:
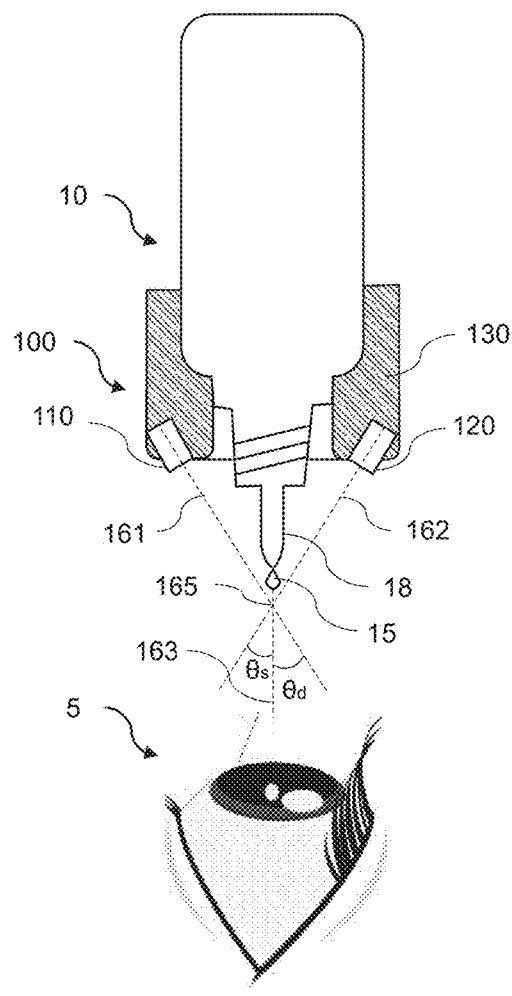
FIG. 2 is a partial cutaway view of a drop dispenser with a drop detection device shown detecting a drop being dispensed into a patient's eye, according to an embodiment of the present disclosure.

FIG. 2 is a cut-away view of a drop detection device 100 coupled to an eye dropper 10, according to one embodiment of the present disclosure. The drop detection device 100 includes light detector 110 and a light source 120 coupled to or integrated into a housing 130. The light detector 110 is coupled to the housing 130 and oriented to receive light rays along a detection axis 161 at a detection angle $\theta_d$ relative to a dispensing axis 163 of the dropper 10, which may also be described as a central axis of the drop detection device 100. The light source 120 is coupled to the housing 130 and oriented to emit light rays along an emission axis 162 at an emission angle $\theta_s$ relative to the dispensing axis 163. The housing 130 may comprise an annular body, wherein the dropper 10 can be received within a central lumen of the housing 130. It may be desirable for the detection axis 161 to intersect with the light source's emission axis 162 at the dispensing axis 163. The advantage of this approach is that both the detector 110 and the light source 120 can be oriented at an oblique angle, even a steep angle, to the horizontal such that there is no hardware beyond the dispensing tip. In the illustrated embodiment, the angle between the normals to the light source 120 and detector 110 may be made smaller and may depend, at least in part, by the contours of the dropper 10. The dropper 10 is shown received within the drop detection device 100. However, in some embodiments, the drop dispenser 10 and drop detection device 100 comprise an integral body.

In the embodiment of FIG. 2, the light source 120 and light detector 110, focusing optics, and/or filters are coupled, mounted, or otherwise positioned in or on the housing 130, which is configured to couple to or receive the dropper 10. The detection device 100 is coupled to the drop dispenser 10 such that the light detector 110 and the light source 120 are positioned above or proximal to the dispensing tip 18. Such an arrangement may be beneficial because it allows a patient or physician to administer drops without the components of the device 100 interfering with the treatment. In some embodiments, the light source 120 and light detection 110 components are coupled to a dispensing tip of a dropper. Further, while the light source 120 and light detector 110 are shown on opposite sides of the dispensing axis 163, in some embodiments, the light source 120 and light detector 110 are positioned on a same side of the dispensing axis 163. Further still, the light source 120 and/or light detector 110 can be positioned or oriented at angles different from those shown in FIG. 1, such as narrower or wider angles. In some embodiments, $\theta_d$ and $\theta_s$ have an equal or substantially equal absolute value. In other embodiments, $\theta_d$ and $\theta_s$ have different absolute values. In some embodiments, the light source 120 and/or the light detector 110 are oriented at an angle that is coming out of the page in FIG. 2.

It will be understood that, although the light detector 110 and light source 120 are shown on opposite sides of the dispensing axis 163, the light detector 110 and light source 120 may not be on opposite sides of the dispensing axis 163, in some embodiments. For example, in some embodiments, the light detector 110 and the light source 120 are adjacent one another. In some embodiments, the light detector 110 and light source 120 are positioned at 30°, 60°, 90°, 120°, or any other suitable angle relative to one another and with respect to the dispensing axis 163.

A drop 15 from the dropper 10 travels along the dispensing axis 163 and crosses an interrogation point 165, which is the point of intersection between the emitting axis 162 of the light detector 110 and the dispensing axis 163. At the intersection point 165, light rays from the light source 120 are scattered, reflected, and/or refracted by the drop 15, and a portion of the light rays from the light source are redirected toward the light detector 110 along the detection axis 161. The light detector 110 receives a reflected portion of light and generates a signal in response to the received light. The signal generated may indicate the presence of a drop via a change in voltage, current, impedance, or any other suitable electrical characteristic.

As explained further below, in some embodiments, the signal may be analyzed by a processing system or a processing component to identify when the drop 15 has passed the interrogation point 165. Accordingly, the signals generated by the light detector 110 can be analyzed to determine that the drop 15 has been dispensed to the eye 5, when the drop 15 was dispensed, how many drops were dispensed, and/or the size of the drop(s) dispensed.

In practice, the scattered light detected by the light detector 110 may be relatively weak and may be generated across a wide solid angle. To improve the signal-to-noise ratio (SNR) of the system, several approaches can be employed. First, the light detector 110 and light source 120 can be coupled, mounted, positioned, or otherwise arranged with respect to the dropper 10 such that the intersection point 165 on the dispensing axis 163 is close to the dispensing tip 18, to avoid the detector 110 collecting other sources of backscatter, such as reflections of light beams off the surface of the eye 5. Additionally, having the interrogation point 165 close to the dispensing tip 18 may ensure that the drop 15 intersects with the emission axis 161 even if the dropper 10 is not completely vertical, for example, when the dropper 10 is oriented at an oblique angle.

The wavelength of the light source 120 may be chosen to give a maximum power permitted based on eye safety restrictions, the detector's 110 spectral response, optical properties of the drop 15, and other parameters. The detector 110 may comprise an optical collection subsystem that includes a photodetector and a collection and focusing lens to increase or maximize the amount of light that is captured at the detector 110. This may be particularly advantageous if the light-collecting area of the detector 110 is small. A bandpass filter can also be used to reject some or all of the ambient light, and/or wavelengths of the beam from the light source 120 that are less desirable for analysis.

Figure 3A:
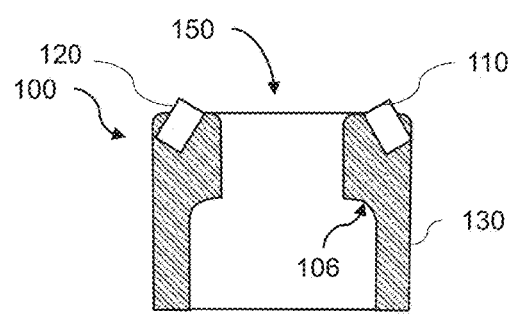
FIGS. 3A and 3B include a cross-sectional view and a top plan view, respectively, of the drop detection device shown in FIG. 2, taken along the line A-A, according to aspects of the present disclosure.
Figure 3B:
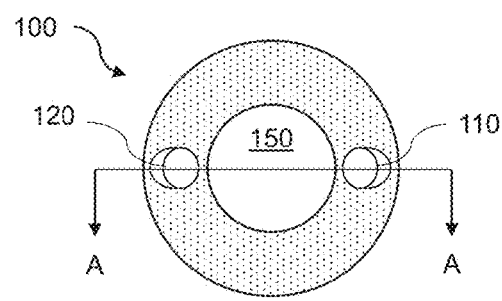

FIG. 3A illustrates a side cross-sectional view of the drop detection device 100 according to the embodiment shown in FIG. 2. The device 100 includes the light detector 110 and the light source 110 coupled to a housing 130 that is configured to receive the eye dropper 10. The housing may include a cylindrical body with a central lumen 150 configured to receive the dropper 10. An inner surface of the housing 130 comprises a lip or shelf 106 configured to engage the lip 16 of the dropper 10, such that the device 100 and the dropper 10 are maintained at relatively stable or fixed positions relative to one another. FIG. 3B is a top view of the device 100 shown in FIG. 3A. As shown in FIG. 3B, the light source 120 and light detector are positioned at approximately the 9 o'clock and 3 o'clock positions, or 0° and 180° positions, on the top of the housing 130 and on opposite sides of the lumen 150.

The light detector 110 and the light source 120 are oriented and positioned to detect light reflected by a drop 15, thereby allowing light source 120 and detector 110 to be placed proximal to the dispensing tip 18. For example, the emission angle $\theta_s$ and/or the detection angle $\theta_d$ may be 45° or less, in some embodiments. However, the emission angle may be any suitable angle, such as 75°, 60°, 45°, 30°, 20°, 10°, etc.

Figure 4:
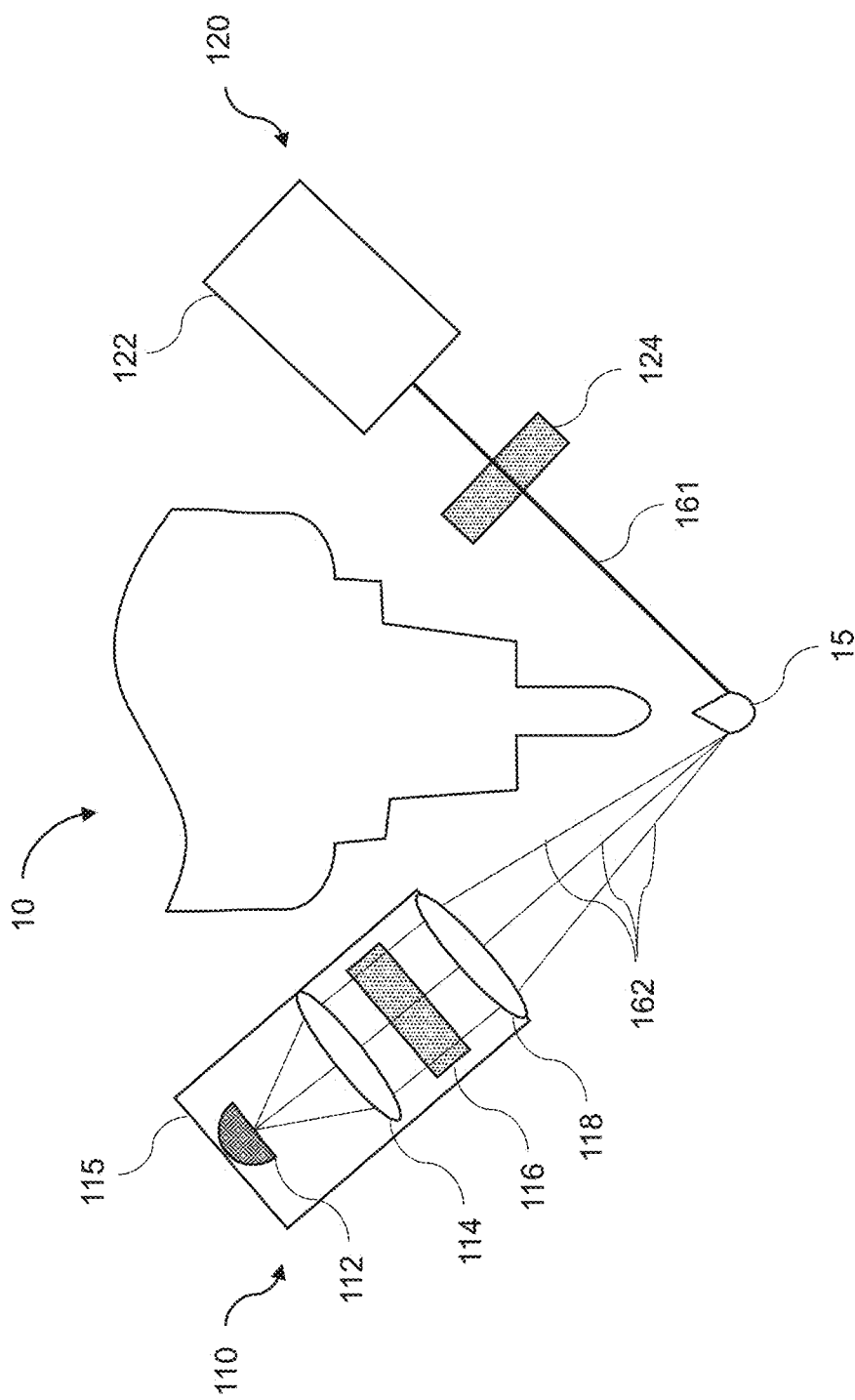
FIG. 4 is a diagrammatic schematic view of a drop detection device, according to aspects of the present disclosure.

FIG. 4 is a diagrammatic view of a drop detection device 100, according to embodiments of the present disclosure. In that regard, the light detector 110 comprises a plurality of optical components contained within a housing 115. Specifically, the light detector 110 comprises a light detection component 112, a focusing lens 114, a spectral filter or bandpass filter 116, and a collimating lens 118. As the light beam from is refracted by the drop 15 along the detection axis 161, the collimating lens 118 collimates the light rays, which then pass through and are filtered by the spectral filter 116. The spectral filter 116 may comprise, for example, a glass substrate with a film configured to allow a certain band of wavelengths to pass through (e.g., IR, near IR), while excluding other types of light (e.g., visible, ultraviolet). However, other types of filters are also contemplated. The filtered light rays then pass to the focusing lens 114, which focuses the light rays onto a collecting surface of the light detection component 112. In some embodiments, the light detection component 112 comprises a photodiode, such as a silicon-based photodiode. However, the light detection component 112 is not limited to photodiodes and may comprise other types of light-detecting transducers.

The light source 120 includes a light emitter 122 and a filter 124. In some embodiments, the light emitter 122 and filter 124 are coupled to or integrated into a housing, similar to the housing 115 of the light detector 110. The light emitter 122 may comprise a laser, such as an IR laser, a light-emitting diode (LED), an incandescent bulb, or any other suitable source of light. In some embodiments, the light source 120 is configured to emit a collimated beam of light along an emission axis 162 toward the drop 15. In some embodiments, the light emitter 122 is configured to emit the beam as a collimated beam. For example, the light emitter 122 may comprise a laser device. In other embodiments, the light emitter 122 may emit a non-collimated light beam, which is collimated or restricted by a filter. For example, in some embodiments, the light emitter 122 comprises a low-cost LED bulb, and the filter 124 is a spatial filter configured to restrict the light beam to a collimated or substantially collimated beam of light. In some embodiments, the spatial filter 124 comprises a plate with a pinhole configured to allow a substantially collimated portion of light through the pinhole to the drop 15. In other embodiments, the light source 120 is not collimated. In some embodiments, a spatial filter may be included in the light detector 110. In some embodiments, the filter 124 comprises a spectral filter configured to limit the beam to a range of wavelengths. In some aspects, by restricting the range of wavelengths to a safe or relatively safe range of wavelengths (e.g., IR), a higher intensity or wattage of light can be used without causing damage to the patient's eye.

Figure 6A:
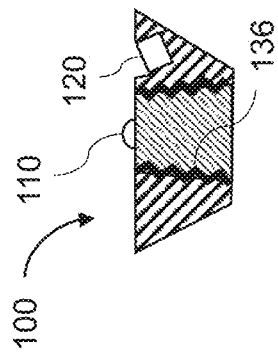
FIGS. 6A and 6B include a cross-sectional view and a top plan view, respectively, of the drop detection device shown in FIG. 5, taken along the line B-B, according to embodiments of the present disclosure.
Figure 6B:
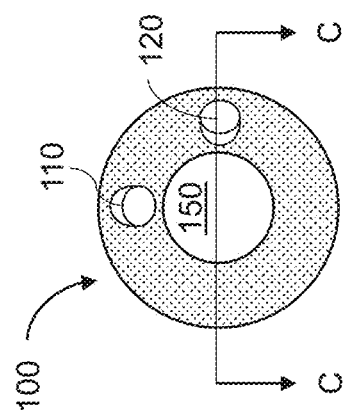
Figure 7A:
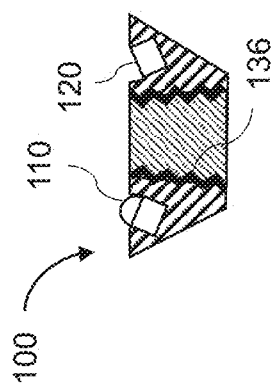
FIGS. 7A and 7B include a cross-sectional view and a top plan view, respectively, of the drop detection device shown in FIG. 5, taken along the line C-C, according to embodiments of the present disclosure.
Figure 7B:
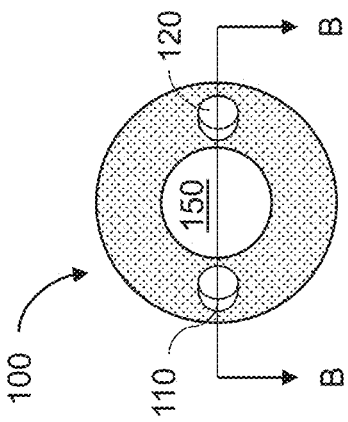
Figure 5:
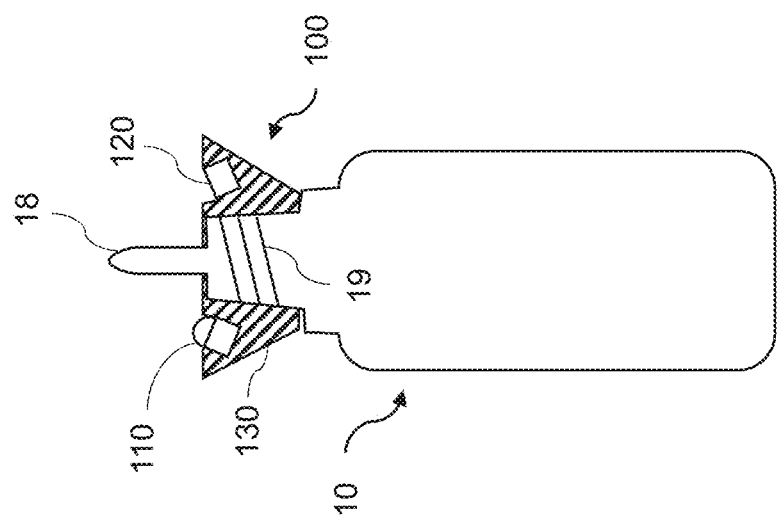
FIG. 5 is a partial cutaway view of a drop dispenser with a drop detection device, according to an embodiment of the present disclosure.

FIG. 5 illustrates a partial cutaway view of a light detection device coupled to an eye dropper, according to another embodiment of the present disclosure. In the embodiment of FIG. 5, the device 100 comprises a housing 130 that is configured to engage threads 19 of a distal or dispensing region of the eye dropper 10. For example, in some embodiments, the device 100 can be coupled to the dropper 10 by removing the cap, and twisting the device 100 onto the threads of the dropper 10. In some embodiments, the device 100 may further comprise a cover or lid to cover and/or seal the dispensing tip, such that the device 100 can replace the cap (e.g., 14, FIG. 1A) of the dropper 10, and allow for the device 100 to be used intermittently without removing the device 100 and replacing the cap between drop applications. FIG. 6A is a cross-sectional view of the device 100 shown in FIG. 5. As shown in FIG. 6A, the device 100 includes threads 136 configured to engage the threads 19 of the device 100. As shown in FIG. 6B, the light detector 110 and light source 120 are shown at opposite sides of the lumen 150 of the device 100, at the 9 o'clock (180°) and 3 o'clock (0°) positions, respectively. FIGS. 7A and 7B show a different embodiment of a drop detection device 100, with the light detector 110 and light source 120 at different positions. In that regard, as shown in FIG. 7B, the light detector 120 is at the 12 o'clock position (90°), and the light source 120 is at the 3 o'clock position (0°). In other embodiments, the light source 120 and/or light detector 110 can be positioned at any suitable position relative to one another such that the detector 110 can collect at least a portion of the light refracted from the drop 15.

Figures 8A, 8B:
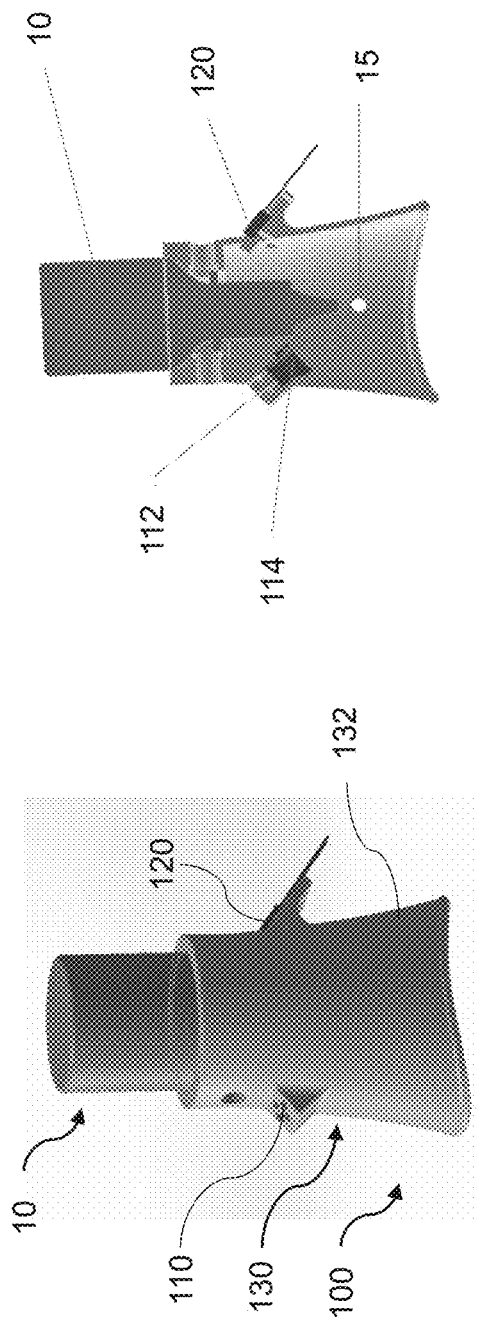
FIG. 8A is a perspective view of a drop dispenser with a drop detection device, according to an embodiment of the present disclosure.
FIG. 8B is a cross-sectional view of a drop dispenser with a drop detection device, according to an embodiment of the present disclosure.

FIGS. 8A and 8B show a drop detection device 100 coupled to an eye dropper 10, according to another embodiment of the present disclosure. In the embodiment of FIG. 8A, the light detector 110 and light source 120 are coupled to a housing 130 that includes a cup or shroud portion 132 that extends distally of the dispensing portion of the dropper 10. The shroud portion 132 can facilitate proper spacing and positioning of the device 100 relative to the patient's eye, and/or block ambient light from reaching the light detector 110.

As shown in FIG. 8B, the collecting lens 114 of the light detector is positioned on an interior of the shroud portion 132, and oriented at an oblique angle relative to the dispensing axis of the dropper 10. The light collecting element 112 (e.g., photodiode) bulges out of the shroud portion 132. The light source 120, which may include a laser, laser diode, LED, or other suitable light source, is positioned to emit light in the interior of the shroud portion 132 of the housing 130 at an oblique angle relative to the dispensing axis of the dropper 10.

Figure 9A:
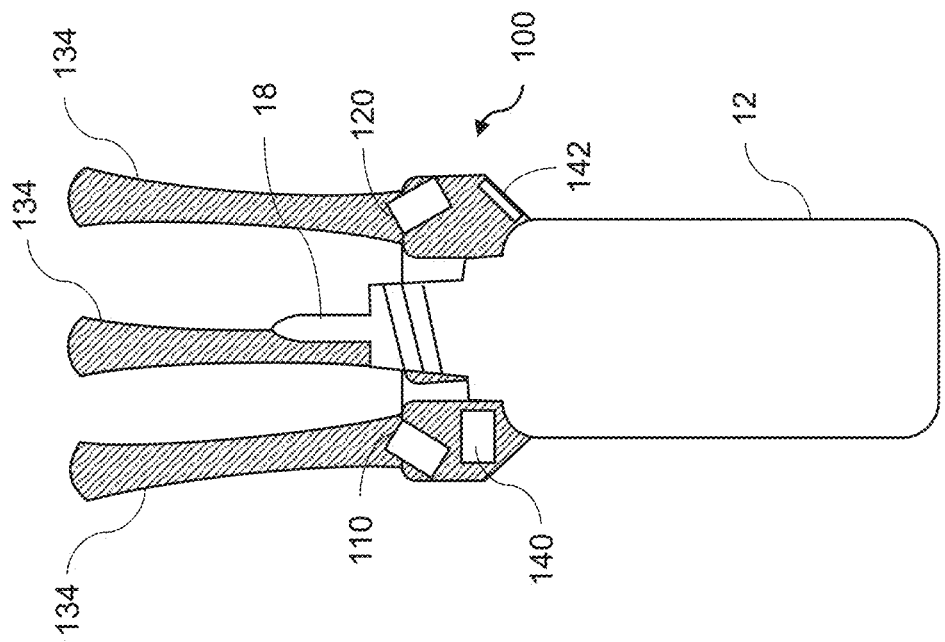
FIGS. 9A and 9B are partial cutaway views of a drop dispenser with a drop detection device, according to an embodiment of the present disclosure.
Figure 9B:
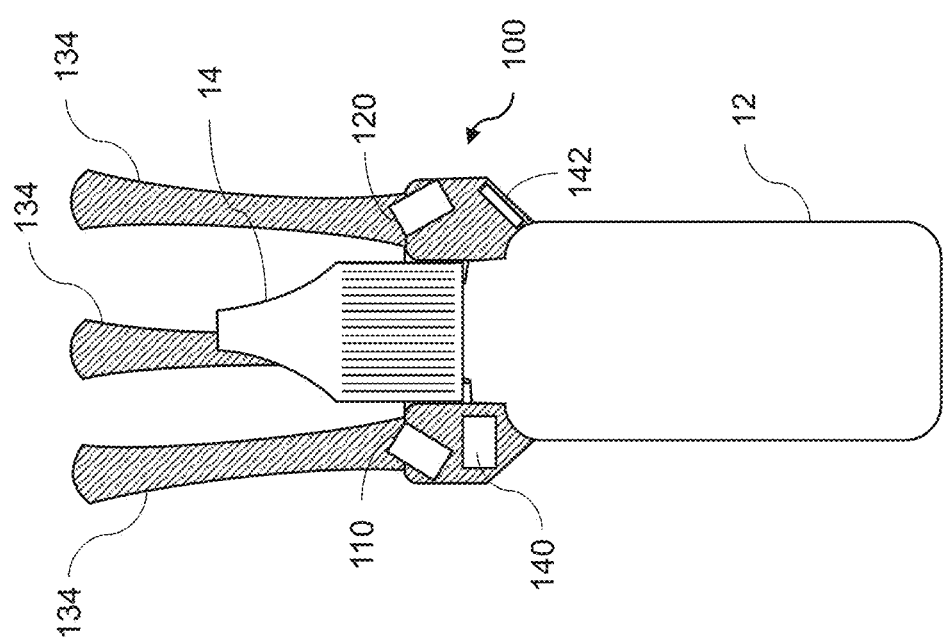

In FIGS. 9A and 9B, a drop detection device 100 according to another embodiment is shown coupled to an eye dropper. As shown in FIG. 9A, the device 100 includes three positioning arms 134 positioned around the periphery of the device and protruding distally of the distal dispensing portion of the dropper 10. The positioning arms 134 are configured to facilitate appropriate positioning of the eye dropper 10 relative to the patient's eye, without restricting access to the cap 14. In that regard, the spacing between the arms 134 provides access for a user to unscrew or otherwise remove the cap 14, as shown in FIG. 9B, and replace the cap when the user is done using the device 100, as shown in FIG. 9A. It will be understood that, in some embodiments, the device 100 may include fewer or more positioning arms than the embodiment shown in FIGS. 9A and 9B. For example, the device 100 may include 1, 2, 3, 4, 5, 6, or more positioning arms 134. Further, the positioning arms may extend more or less distally than the embodiment shown in FIGS. 9A and 9B. In some embodiments, the positioning arms are integrally formed with the housing of the device 100. In other embodiments, the positioning arms 134 are separate components that are coupled to the housing 100. In some embodiments, the arms 134 are formed of a flexible polymer material, such as silicone, rubber, or plastic. In other embodiments, the arms 134 are formed of a more rigid material, such as metal, fiberglass, or a rigid plastic. The arms are positioned such that they do not interfere with the emitting and receiving axes of the light source 120 and the light detector 110.

Additionally, FIGS. 9A and 9B show a processing circuit 140 and a battery 142 coupled to the housing 130 of the device 100. The processing circuit 140 may comprise a plurality of analog and/or digital electronic components configured to filter and/or manipulate signal data, detect drops, initiate a detection sequence, store data to a memory, communicate data to a separate computing device, and perform any suitable processing step. The battery 142 is configured to provide power to the processing circuit 140. It will be understood that, although the battery 142 and the processing circuit 140 are shown as separate components, the battery 142 and the processing circuit 140 may be positioned together, such that the battery is in physical contact with the processing circuitry of the processing circuit 140.

Figure 10:
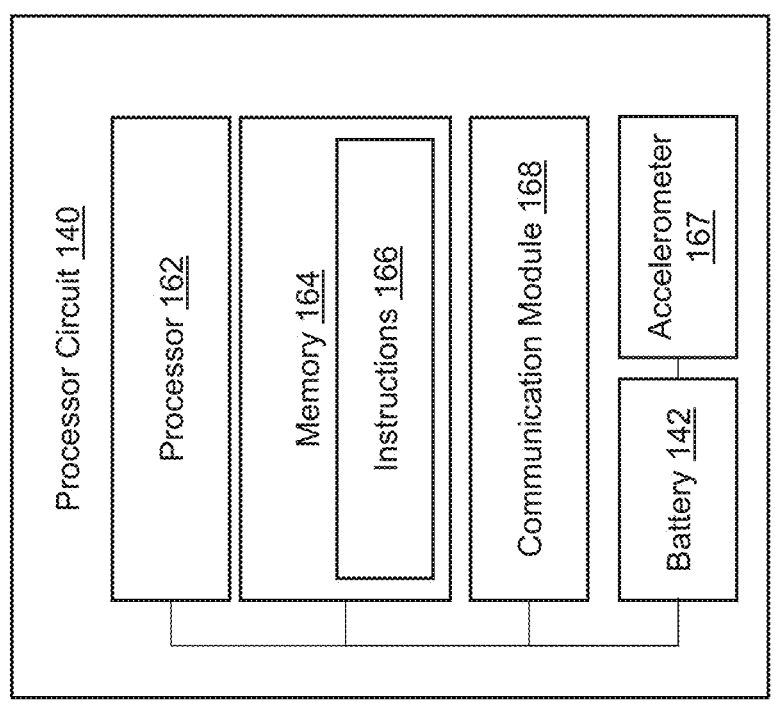
FIG. 10 is a diagrammatic schematic view of a processor circuit of a drop detection device, according to an embodiment of the present disclosure.

A schematic diagram of the processing circuitry 140 and battery 142 is shown in FIG. 10. As shown, the processor circuit 140 may include a processor 162, a memory 164, and a communication module 168. These elements may be in direct or indirect communication with each other, for example via one or more buses.

The processor 162 may include a central processing unit (CPU), a digital signal processor (DSP), an ASIC, a controller, an FPGA, another hardware device, a firmware device, or any combination thereof configured to perform the operations described herein. The processor 162 may also be implemented as a combination of computing devices, e.g., a combination of a DSP and a microprocessor, a plurality of microprocessors, one or more microprocessors in conjunction with a DSP core, or any other such configuration.

The memory 164 may include a cache memory (e.g., a cache memory of the processor 162), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 164 includes a non-transitory computer-readable medium. The memory 164 may store instructions 166. The instructions 166 may include instructions that, when executed by the processor 162, cause the processor 162 to perform the operations described herein with reference to FIGS. 4 and 11. Instructions 166 may also be referred to as code. The terms "instructions" and "code" should be interpreted broadly to include any type of computer-readable statement(s). For example, the terms instructions and code may refer to one or more programs, routines, sub-routines, functions, procedures, etc. Instructions and code may include a single computer-readable statement or many computer-readable statements.

The communication module 168 can include any electronic circuitry and/or logic circuitry to facilitate direct or indirect communication of data between the processor circuit 140 and a remote computing device. In that regard, the communication module 168 can be an input/output (I/O) device. In some instances, the communication module 168 facilitates direct or indirect communication between various elements of the processor circuit 140 and/or a separate computing device, such as a database, a laptop, a smartphone, a tablet, or any other suitable computing device. For example, the communication module 168 may facilitate wired and/or wired communication means (e.g., USB, Bluetooth, Wi-Fi) to transmit backscatter signal data or other drop detection data to a mobile computing device for analysis and/or communication to another entity, such as a physician's computing system or mobile computing device. The processing circuit 140 may further include a battery 142 or other charge storage device to provide electrical power to the components of the processing circuit, light source 120, and/or light detector 110. The battery 142 may be sized and configured to provide power to the components of the device 100 for hours, days, or weeks of use. In some embodiments, the processing circuit 140 includes a rechargeable battery and a charge port or power port for recharging the battery and/or providing electrical power to the components of the processing circuit 140, the light detector 110, and/or the light source 120. In that regard, in some embodiments, the device 100 includes a wired power connection in place of the battery 142. In some embodiments, the battery is not rechargeable, but is configured to be replaced when the battery is depleted (e.g., a coin battery). In that regard, the replaceable battery may be positioned within a portion of the housing that facilitates simple replacement.

In the embodiment of FIG. 10, the processing circuit 140 further includes an accelerometer 167 configured to detect motion and/or the orientation of the device 100. For example, in some embodiments, the accelerometer 167 is configured to detect motion to initiate a drop detection protocol. In other embodiments, the accelerometer 167 is configured to determine an angle at which the device 100 and/or dropper 10 is oriented. Data indicating the angle of the dropper 10 can be used to adjust calculations and detections made by the detector 110 and processing circuit 140 based on the angle of the dropper 10 and/or device 100. For example, when the device 100 and/or dropper 10 is oriented at an oblique angle and is not vertical, the device 100 may detect scattered light from a drop for a longer period of time that it would have detected if the dropper 10 were oriented vertically. Accordingly, the processing circuit can adjust the data (e.g., size of the drop) to account for the oblique angle of the dropper 10.

Figure 11:
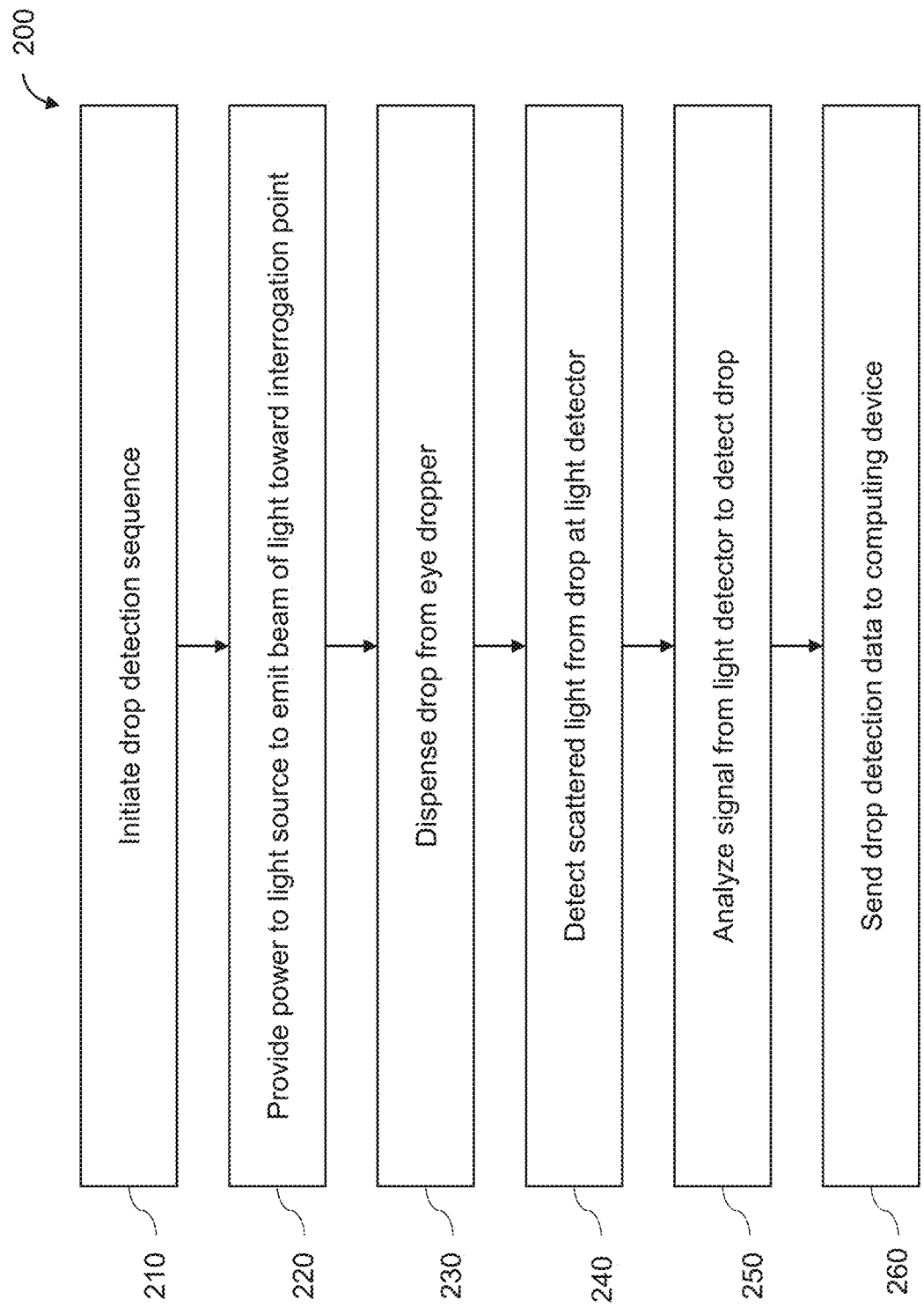
FIG. 11 is a flow diagram illustrating a method of detecting a drop using a drop detection device, according to an embodiment of the present disclosure.

FIG. 11 is a flow diagram of a method 200 for detecting drops using a drop detection device 100. In step 210, the drop detection sequence is initiated. In some embodiments, the drop detection sequence may be initiated by pressing a button, flipping a switch, tapping the device, or providing any suitable input for initiating the drop detection sequence. In some embodiments, the accelerometer 167 may be configured to detect motion of the device 100, such as when the device 100 is picked up by a user, and the processing circuit 140 is configured to automatically initiate the drop detection sequence in response to receiving a signal from the accelerometer indicating motion. In other embodiments, the drop detection sequence may initiate upon providing power to one or more of the light source 120, the light detector 110, and/or the processing circuit 140, without receiving any additional input to start the sequence.

Upon initiating the sequence, power is provided to the light source in step 220 to emit a beam of light toward an interrogation point. As explained above, the light source may comprise a laser, laser diode, an LED, an incandescent bulb, or any other suitable light source. The beam may comprise a range of wavelengths, for example, between about 500 nm and about 1100 nm. In an exemplary embodiment, the beam may comprise a center wavelength at between 700 nm and 1000 nm. For example, a drop detection device may include a low-cost VCSEL operating at 850 nm as the center wavelength of the beam, and may operate at <1 mW optical power, for example, 120 uW of optical power. However, in other embodiments, the light source operates at other wavelengths or ranges of wavelengths, including portions or bands of the visible light spectrum, near-IR, and IR. For example, wavelengths at or near 500 nm, 600 nm, 700 nm, 900 nm, 1 um, or any other suitable wavelength may be used to detect drops from the drop dispensing device. In some aspects, the range of wavelengths of the beam and/or the center wavelength or frequency of the beam can be selected or configured based on at least one of the optical properties of the drops of fluid to be dispensed, the sensitivity profile of the light detector, and safety restrictions for the user's eye. Further, in some embodiments, the light source may operate at optical powers other than 120 uW, including 50 uW, 75 uW, 150 uW, 200 uW, 500 uW, 1.5 mW, 2 mW, 5 mW, or any other suitable amount of optical power.

In some embodiments, two or more light sources may be used to emit beams of different frequency ranges. Based on a comparison of the scattered light of the two separate ranges, the color and/or makeup of the drop may be determined.

In step 230, a drop is dispensed from the eye dropper to the user's eye. The drop may be dispensed by squeezing the dropper bottle, pressing a button, depressing a plunger or a pump, or any other suitable method. In some embodiments, the size of the drop is relatively stable or fixed based on the geometry of the dispensing tip. In other embodiments, the size of the drop can be adjusted or controlled by the user. In step 240, the light detector receives and detects light from the light source that is scattered from the dispensed drop. As explained above, in an exemplary embodiment, the beam of light meets the drop at an interrogation point that is proximate the dispensing tip, and the light detector may be oriented to receive sufficient scattered light from the interrogation point to detect the drop. The light detector may comprise a low-cost photodetector, such as a photodiode. A lens may be placed in front of the photodetector to increase light collection. In some embodiments, a resistor may be used as a transimpedance amplifier for the signal. In other embodiments, multiple resistors and/or other electronic components may be used as a transimpedance amplifier. The photodetector may be configured to generate a signal based on the detected light, in which a measured voltage, current, or impedance indicates the intensity or amount of scattered light received at the photodetector. In an exemplary embodiment, the signal comprises a time-varying voltage, in which the voltage represents the intensity or amount of detected scattered light from the drop.

In step 250, the signal is analyzed to determine that a drop has been dispensed. In some embodiments, the analysis may be performed using digital and/or analog electrical components comprising part of a processing circuit of the drop detection device. For example, the processing circuit may include an analog-to-digital converter, capacitors, resistors, inductors, analog gates, etc. The analysis may comprise determining when the signal from the detector exceeds a threshold voltage for a predetermined period of time (i.e. a standoff time), using envelope detection, data transforms, etc. In some embodiments, the analysis comprises compensating for a background signal by, for example, subtracting or reducing the background signal from the measured data. In some embodiments, an analog or digital low-pass filter is coupled to the detector and configured to filter the raw signal data before processing to remove or reduce spikes or noise in the data. In other embodiments, the raw data is not analyzed at a processing circuit of the device, but is instead communicated to a separate computing device (e.g. a server, laptop, tablet, laptop) for analysis to detect the drop. In some embodiments, the raw data is stored to a memory device of the drop detection device before analysis. In some embodiments, the results of the analysis (e.g., number, time of dispensed drops) is stored to the memory device. In step 260, the drop detection data is sent to a computing device or system. The data may be detector signal data (e.g., time trace), or the data may comprise the results of analyzed detector signal data, such as the number of drops, drop volume, or time of drop. The drop information may be transmitted by bluetooth, Wi-Fi, BLE, NFC, USB, or other wired or wireless connectivity. The remote device may be a mobile device or a cloud connected computer. Drop information may be stored and made available to a user, caregiver or physician to monitor compliance with drug dosing instructions and/or adjust treatment.

It will be understood that various modifications can be made to the method described above without straying from the scope of the present disclosure. For example, in some embodiments, the drop detection device includes an alarm or feedback component configured to indicate to the user that a drop has been dispensed and detected. The feedback component may include a light bulb, a speaker, a haptic feedback device, etc. The feedback component may be triggered to alert the user of the detection of a drop based on a signal received from the processing circuit that indicates that the drop has been detected.

Figure 12:
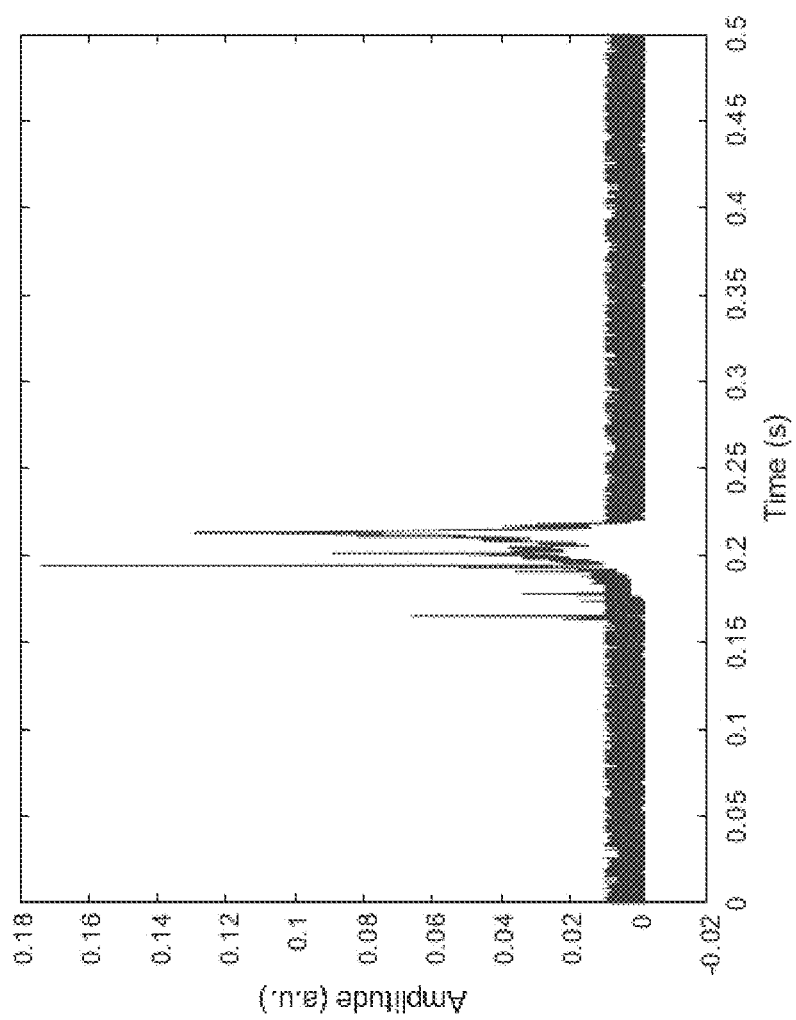
FIG. 12 is a graph showing a time trace of a drop detector during the dispensing of a drop, according to an embodiment of the present disclosure.

FIG. 12 is a graph of the time trace from the light detector showing the detection of a drop at approximately 0.2 s. Approximately 120 uW of effective laser power was used, which may be safe for the eye. The time trace shown in FIG. 12 was obtained using green light from the light source to better visualize the change in amplitude due to the detected drop. In other embodiments, near-IR may be used since the patient would not see the beam and many detectors have higher responsivities at the longer wavelengths.

In addition to determining the presence of a drop, the analyzed signal could be used to determine the number of drops or even the size of the drop. For example, the size of the drop may be determined by the processing circuit based on the amplitude and/or duration of the signal from the detector that rises above a threshold. Further, as explained above, in some embodiments, an accelerometer may be employed to account for the angle of the dropper relative to vertical or normal. The droplet detection mechanism could be used in conjunction with a camera within the dropper that is pointed towards the eye to determine if the droplet entered the eye. As mentioned above, the analysis may be performed using a processing system or circuit that is positioned on the drop detection device. In other embodiments, the data (e.g., time trace) from the detector is transmitted to a separate or remote processor and analysis is performed at the separate processor.

Figure 13:
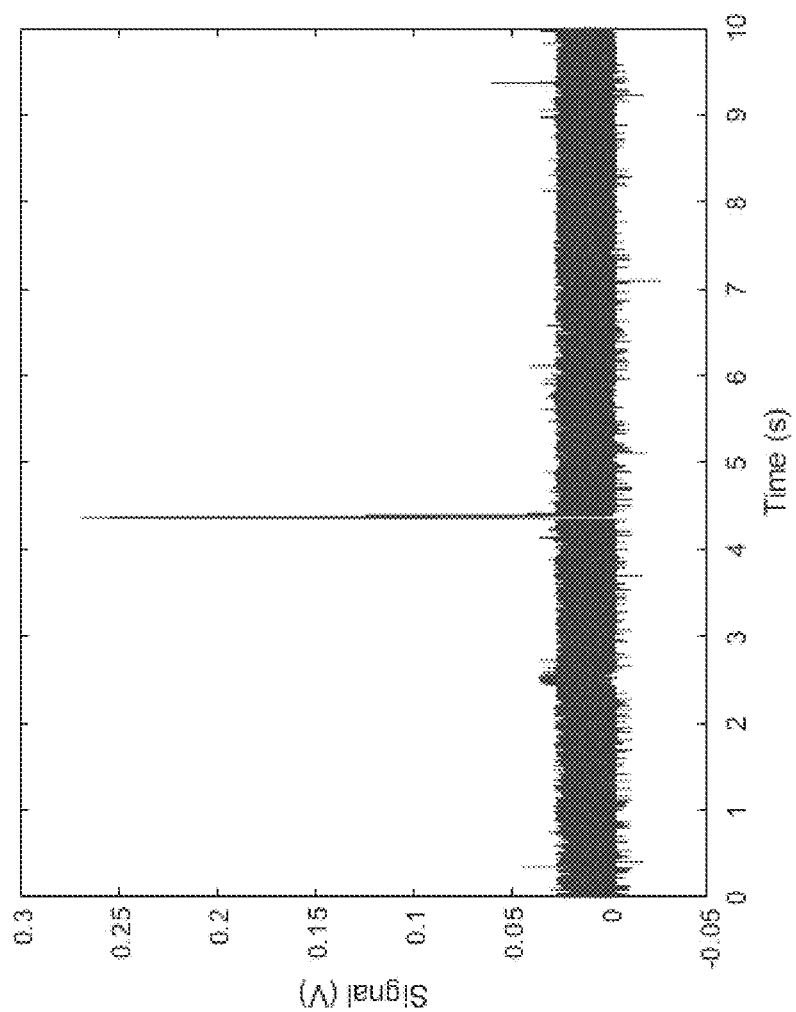
FIG. 13 is a graph showing a time trace of a drop detector during the dispensing of a drop, according to an embodiment of the present disclosure.
Figure 14:
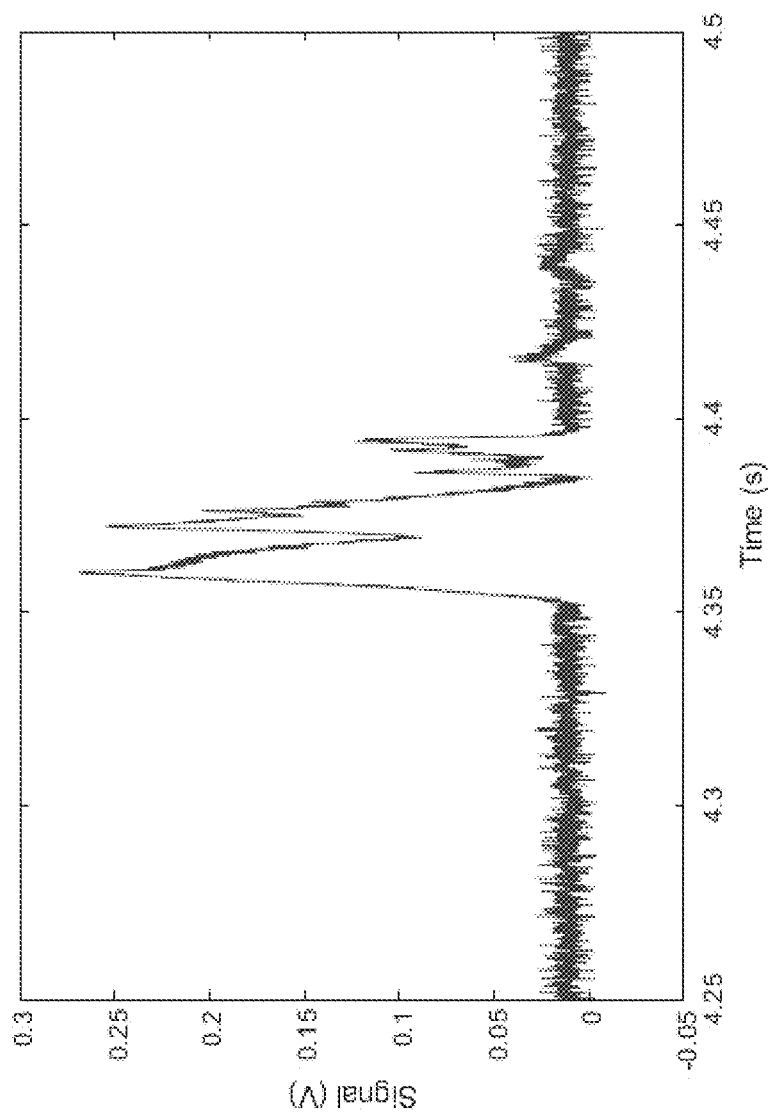
FIG. 14 is a graph showing a time trace of a drop detector during the dispensing of a drop, according to an embodiment of the present disclosure.

FIG. 13 shows the trace from a single drop being dispensed over a 10 second period with improved SNR. The y-axis represents the signal in volts (V), and the x-axis represents the time. A single drop is detected around 4.35 s. FIG. 14 shows the same trace but zoomed in to observe the temporal structure of the signal during the drop more carefully. In some embodiments, the drop detection device is configured to detect droplets at least within 60 ms of each other (supported by width of signal in FIG. 14).

Figure 15:
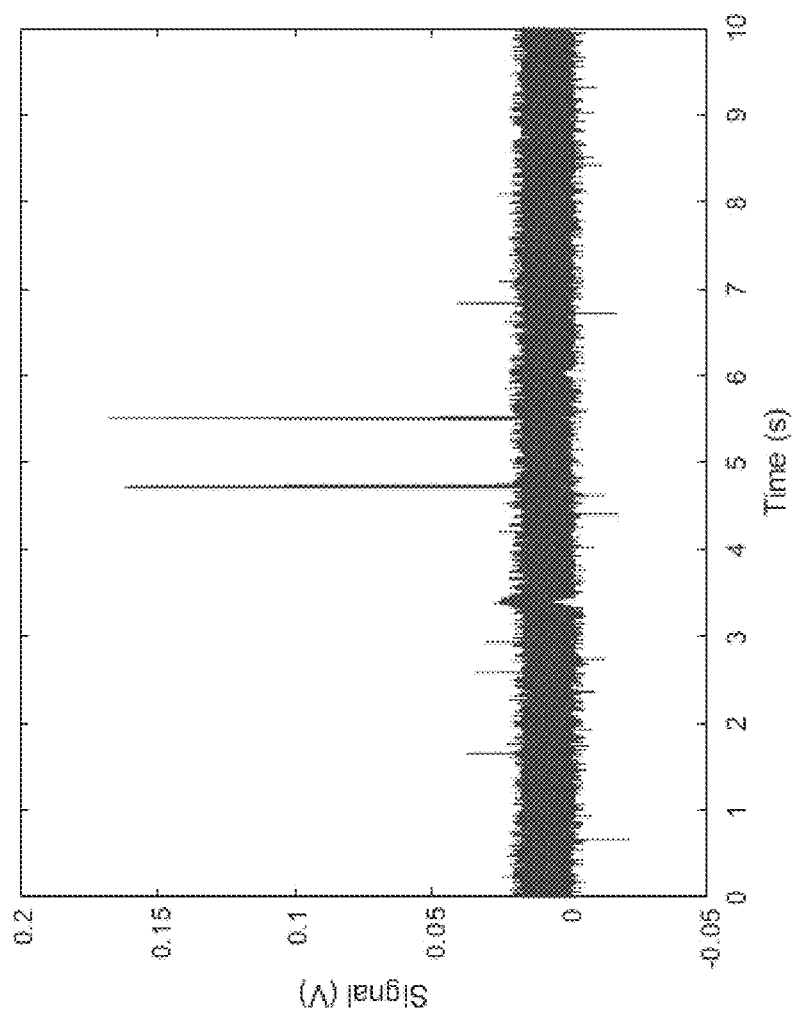
FIG. 15 is a graph showing a time trace of a drop detector during the dispensing of a drop, according to an embodiment of the present disclosure.

FIG. 15 shows a time trace from a photodiode (e.g., the light detector shown in FIG. 1, 2, 3A, or 3B) illustrating the application of two drops. A threshold of 0.07 V may be used to discriminate noise due to eyelashes, ambient lighting, etc. from the droplet signal.

The language herein should be interpreted as illustrative rather than limiting. Accordingly, the logical elements making up the embodiments of the technology described herein are referred to variously as operations, steps, objects, elements, components, or modules. Furthermore, it should be understood that these may be arranged in any order, unless a specific order is inherently necessitated by the embodiments described. For example, in some embodiments, an LED and a long pinhole can be used as the light detector to deliver low-divergence light to the droplet. Further, in some embodiments, the light source could include a spectrally-filtered LED, which may be implemented by including a bandpass filter at or after the light source. The spectrally-filtered LED may be used in combination with spatially-filtered LED lighting techniques. Spectrally filtering the light source may increase the amount of usable light given the constraints of eye safety, comfort, etc. In some embodiments, no lenses are used on the light detector and lower thresholds are adopted. In some embodiments, instead of a photodiode, an avalanche photodiode (APD) can be used to increase sensitivity, although any suitable photodiode or light detector could also be used. The light detector could operate either under reverse bias or unbiased.

Generally, any creation, storage, processing, and/or exchange of user data associated with the method, apparatus, and/or system disclosed herein is configured to comply with a variety of privacy settings and security protocols and prevailing data regulations, consistent with treating confidentiality and integrity of user data as an important matter. For example, the apparatus and/or the system may include a module that implements information security controls to comply with a number of standards and/or other agreements. In some embodiments, the module receives a privacy setting selection from the user and implements controls to comply with the selected privacy setting. In other embodiments, the module identifies data that is considered sensitive, encrypts data according to any appropriate and well-known method in the art, replaces sensitive data with codes to pseudonymize the data, and otherwise ensures compliance with selected privacy settings and data security requirements and regulations.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A device for detecting a drop dispensed by a drop dispenser, comprising:
    a housing configured to couple to the drop dispenser;
    a light source coupled to the housing and configured to emit a beam of light toward the drop dispensed by the drop dispenser;
    a processing circuit; and
    a light detector coupled to the housing and in communication with the processing circuit,
    the light detector configured to:
        receive a portion of the beam of light reflected by the drop; and
        provide, to the processing circuit, a signal indicating an amount of reflected light received over a period of time, wherein the processing circuit is configured to detect the drop based on the signal, wherein the light source and the light detector are disposed on a distal-facing surface of the housing, wherein the distal-facing surface of the housing is arranged perpendicularly to a dispensing axis of the drop dispenser and is proximal to a distal end of the drop dispenser when the drop dispenser is coupled to the housing; and, wherein the light source and the light detector are coupled to the housing such that, when the housing is coupled to the drop dispenser:

the light source is oriented to emit the beam of light along a first axis at a first oblique angle relative to the dispensing axis of the drop dispenser, and the light detector is oriented to receive the portion of the beam of light along a second axis at a second oblique angle relative to the dispensing axis of the drop dispenser, wherein the second oblique angle is non-parallel to the first oblique angle.

2. The device of claim 1, wherein the light source comprises at least one of a laser diode and a light-emitting diode.

3. The device of claim 1, wherein the light detector comprises a photodiode.

4. The device of claim 1, wherein the light detector comprises a bandpass filter and a focusing lens.

5. The device of claim 1, wherein the first axis, the second axis, and the dispensing axis intersect at an interrogation point located distally of a dispensing tip of the drop dispenser.

6. The device of claim 1, wherein the housing is configured to engage a lip of the drop dispenser.

7. The device of claim 6, wherein the housing is coupled to the drop dispenser such that a cap of the drop dispenser can be removed and replaced without removing the drop dispenser.

8. The device of claim 1, wherein the processing circuit is configured to detect the drop by determining that an amplitude of the signal exceeds a threshold for a predetermined amount of time.

9. A method for detecting a drop dispensed by a drop dispenser, including:

emitting, by a light source disposed on a distal-facing surface of the drop dispenser, a beam of light toward the drop, wherein the light source is oriented to emit the beam of light along a first axis at a first oblique angle relative to a dispensing axis of the drop dispenser, wherein the distal-facing surface is arranged perpendicularly to the dispensing axis of the drop dispenser and is proximal to a distal end of the drop dispenser;

receiving, by a light detector disposed on the distal-facing surface of the drop dispenser, a portion of the beam of light reflected by the drop, wherein the light detector is oriented to receive a portion of the beam of light along a second axis at a second oblique angle relative to the dispensing axis of the drop dispenser, wherein the second oblique angle is non-parallel to the first oblique angle;

providing, by the light detector, a signal indicating an amount of reflected light received by the light detector over a period of time; and analyzing, by a processing component in communication with the light detector, the signal to detect the drop.

10. The method of claim 9, wherein emitting the beam of light comprises emitting the beam of light using at least one of a laser diode or a light-emitting diode.

11. The method of claim 9, wherein receiving the portion of the beam of light comprises receiving the portion of the beam of light using a photodiode.

12. The method of claim 9, wherein the light detector comprises a bandpass filter and a focusing lens.

13. The method of claim 9, wherein the first axis, the second axis, and the dispensing axis intersect at an interrogation point located distally of a dispensing tip of the drop dispenser.

14. The method of claim 9, wherein analyzing the signal to detect the drop comprises determining that an amplitude of the signal exceeds a threshold for a predetermined amount of time.

15. A device for detecting a drop dispensed by a drop dispenser, comprising:

a housing configured to couple to the drop dispenser;

a light source coupled to the housing and configured to emit a beam of light toward the drop dispensed by the drop dispenser;

a processing circuit; and a light detector coupled to the housing and in communication with the processing circuit, the light detector configured to:

receive a portion of the beam of light reflected by the drop: and provide, to the processing circuit, a signal indicating an amount of reflected light received over a period of time, wherein the processing circuit is configured to detect the drop based on the signal, wherein the light source and the light detector are coupled to a lip of the housing and are located on a plane perpendicular to a dispensing axis, wherein, during measurement of the drop, the light source and the light detector are above a dispensing tip and are configured to detect the drop when the drop is below the dispensing tip wherein the light source and the light detector are coupled to the lip of the housing such that, when the housing is coupled to the drop dispenser:

the light source is oriented to emit the beam of light along a first axis at a first oblique angle relative to the dispensing axis of the drop dispenser, and the light detector is oriented to receive the portion of the beam of light along a second axis at a second oblique angle relative to the dispensing axis of the drop dispenser, wherein the second oblique angle is non-parallel to the first oblique angle.

16. The device of claim 15, wherein the first axis, the second axis, and the dispensing axis intersect at an interrogation point located below the dispensing tip of the drop dispenser.

17. The device of claim 15, wherein the housing is configured to engage a lip of the drop dispenser.

* * * * *